United States Patent
Gupta et al.

(10) Patent No.: US 9,052,346 B2
(45) Date of Patent: Jun. 9, 2015

(54) SYSTEMS AND METHODS FOR OBTAINING AND USING INCIDENT FIELD TRANSFER FUNCTIONS OF ELECTRICAL STIMULATION SYSTEMS

(71) Applicant: Boston Scientific Neuromodulation Corporation, Valencia, CA (US)

(72) Inventors: Gaurav Gupta, Valencia, CA (US); Joseph M. Bocek, Seattle, WA (US); Ross Daniel Venook, Millbrae, CA (US); Matthew Lee McDonald, Pasadena, CA (US); Rafael Carbunaru, Valley Village, CA (US); Chirag M. Patel, Los Angeles, CA (US)

(73) Assignee: Boston Scientific Neuromodulation Corporaton, Valencia, CA (US)

( * ) Notice: Subject to any disclaimer, the term of this patent is extended or adjusted under 35 U.S.C. 154(b) by 163 days.

(21) Appl. No.: 13/801,282

(22) Filed: Mar. 13, 2013

(65) Prior Publication Data

US 2013/0241573 A1    Sep. 19, 2013

Related U.S. Application Data

(60) Provisional application No. 61/611,504, filed on Mar. 15, 2012.

(51) Int. Cl.
- *G01R 31/00* (2006.01)
- *A61N 1/36* (2006.01)
- *A61N 1/08* (2006.01)

(52) U.S. Cl.
CPC ........ *G01R 31/00* (2013.01); *A61N 1/36* (2013.01); *A61N 2001/086* (2013.01)

(58) Field of Classification Search
CPC . A61N 2001/086; A61N 1/05; A61N 1/3718; A61N 1/37; A61N 1/3752; A61N 1/3706; A61N 2001/083; A61N 1/0534; A61N 1/06; A61N 1/08; A61N 1/16; A61N 1/36; A61N 1/36064; A61N 1/36067; A61N 1/36071; A61N 1/36096; A61N 1/3622; A61N 1/365; A61N 1/36514; A61N 1/36542; A61N 1/372; A61N 1/37258; A61N 5/0601; G01R 31/00; G09B 23/28

USPC .............. 324/615–619, 638; 606/33; 702/109
See application file for complete search history.

(56) References Cited

U.S. PATENT DOCUMENTS

| 5,246,000 A | 9/1993 | Ellis et al. |
| 5,514,162 A | 5/1996 | Bornzin et al. |

(Continued)

FOREIGN PATENT DOCUMENTS

WO    2011051094 A1    5/2011

OTHER PUBLICATIONS

International Search Report and Written Opinion for International Application No. PCT/US2013/030970 mailed May 24, 2013.

(Continued)

*Primary Examiner* — Arleen M Vazquez
*Assistant Examiner* — Lee Rodak
(74) *Attorney, Agent, or Firm* — Lowe Graham Jones PLLC; Bruce E. Black (57) ABSTRACT

A method of estimating response of a medical lead to an electromagnetic field includes providing a medical lead having a proximal end, a distal end, a plurality of electrodes disposed along the distal end, a plurality of terminals disposed along the proximal end, and a plurality of conductors extending along the medical lead and electrically coupling the electrodes to the terminals; individually applying a test field at each of a plurality of test positions along the medical lead using at least one excitation probe; for each application of the test field, determining a response to the application of the test field at one or more of the electrodes or terminals; generating a transfer function using a combination of the responses determined for the applications of the test field; and using the transfer function to estimate a response of the medical lead to an electromagnetic field.

22 Claims, 7 Drawing Sheets

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,170,297 B1 * | 1/2007 | Dunsmore ............ 324/534 |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |
| 8,224,450 B2 | 7/2012 | Brase |
| 2005/0165465 A1 | 7/2005 | Pianca et al. |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2008/0243218 A1 * | 10/2008 | Bottomley et al. ........... 607/116 |
| 2011/0160808 A1 | 6/2011 | Lyden et al. |

OTHER PUBLICATIONS

Park et al., Calculation of MRI-Induced Heating of an Implanted Medical Lead Wire With an Electric Field Transfer Function: Journal of Magnetic Resonance Imaging 26:1278-1285 (2007).

* cited by examiner

SYSTEMS AND METHODS FOR OBTAINING AND USING INCIDENT FIELD TRANSFER FUNCTIONS OF ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/611,504 filed on Mar. 15, 2012, which is incorporated herein by reference.

FIELD

The present invention is directed to the area of implantable electrical stimulation systems and methods of making and using the systems. The present invention is also directed to systems and methods for obtaining and using incident field transfer functions of implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems (including, for example, implantable leads and implantable pulse generators) are often incompatible with magnetic resonance imaging ("MRI") due to the large radio frequency ("RF") pulses used during MRI. The RF pulses can generate transient signals in the conductors and electrodes of an implanted lead. The lead captures RF energy and transmits it to the two ends causing at least the following two effects (a) the RF heating at the lead electrode to patient interface (b) damage to the IPG electronics due to conducted RF. Several factors affect the amount of RF energy captured by the lead like incident field, lead design, lead construction, lead shape, lead trajectory, presence of other elements or materials in proximity, lead length, frequency of RF signal, loading at the un-insulated ends, and the like.

BRIEF SUMMARY

One embodiment is a method of estimating response of a medical lead to an electromagnetic field. The method includes providing a medical lead having a proximal end, a distal end, a plurality of electrodes disposed along the distal end, a plurality of terminals disposed along the proximal end, and a plurality of conductors extending along the medical lead and electrically coupling the electrodes to the terminals; individually applying a test field at each of a plurality of test positions along the medical lead using at least one excitation probe; for each application of the test field, determining a response to the application of the test field at one or more of the electrodes or terminals; generating a transfer function using a combination of the responses determined for the applications of the test field; and using the transfer function to estimate a response of the medical lead to an electromagnetic field.

Another embodiment is a non-transitory computer-readable medium having processor-executable instructions for estimating response of a lead to an electromagnetic field. The processor-executable instructions when installed onto a device enable the device to perform actions including individually applying a test field at each of a plurality of test positions along a medical lead using an excitation probe; for each application of the test field, determining a response to the application of the test field at one or more electrodes or terminals of the medical lead; generating a transfer function using a combination of the responses determined for the applications of the test field; and using the transfer function to estimate a response of the medical lead to an electromagnetic field.

Yet another embodiment is a system for estimating response of a medical lead to an electromagnetic field. The system includes at least one excitation probe configured and arranged for providing a test field; at least one response probe configured and arranged for receiving a signal from a lead in response to the test field; and a control/measurement system coupled to the at least one excitation probe and at least one response probe. The control/measurement system includes a processor for executing processor-readable instructions that enable actions, including individually applying a test field at each of a plurality of test positions along a medical lead using the excitation probe; for each application of the test field, determining a response to the application of the test field at one or more electrodes or terminals of the medical lead using the at least one response probe; generating a transfer function using a combination of the responses determined for the applications of the test field; and using the transfer function to estimate a response of the medical lead to an electromagnetic field.

Another embodiment is a method of estimating electromagnetic coupling of a first medical lead to a second medical lead. The method includes providing a first medical lead and a second medical lead, each having a proximal end, a distal end, a plurality of electrodes disposed along the distal end, a plurality of terminals disposed along the proximal end, and a plurality of conductors electrically coupling the electrodes to the terminals; applying a test field to the first medical lead using at least one excitation probe; determining a response to the application of the test field to the first medical lead at one or more of the electrodes or terminals of the second medical lead; generating a transfer function using the response determined for the application of the test field; and using the transfer function to estimate electromagnetic coupling of the first medical lead to the second medical lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to systems and methods for obtaining and using incident field transfer functions of implantable electrical stimulation systems. The transfer function can be used to estimate the response of a lead of an electrical stimulation system to an electromagnetic field. This can be particularly useful for evaluation of the design and properties of implantable leads and associated electrical stimulation systems.

Any medical lead can be evaluated using the systems and methods described herein. These systems and methods are particularly useful for evaluating implantable leads and, in particular, those leads used for implantable electrical stimulation systems. The systems and methods will utilize such leads to illustrate the systems and methods, but it will be understood that the systems and methods can be utilized with other medical leads. Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; and U.S. Patent Applications Publication Nos. 2005/0165465; 2007/0150036; 2007/0219595; 2007/0239243; and 2008/0071320, all of which are incorporated by reference.

Figure 1:
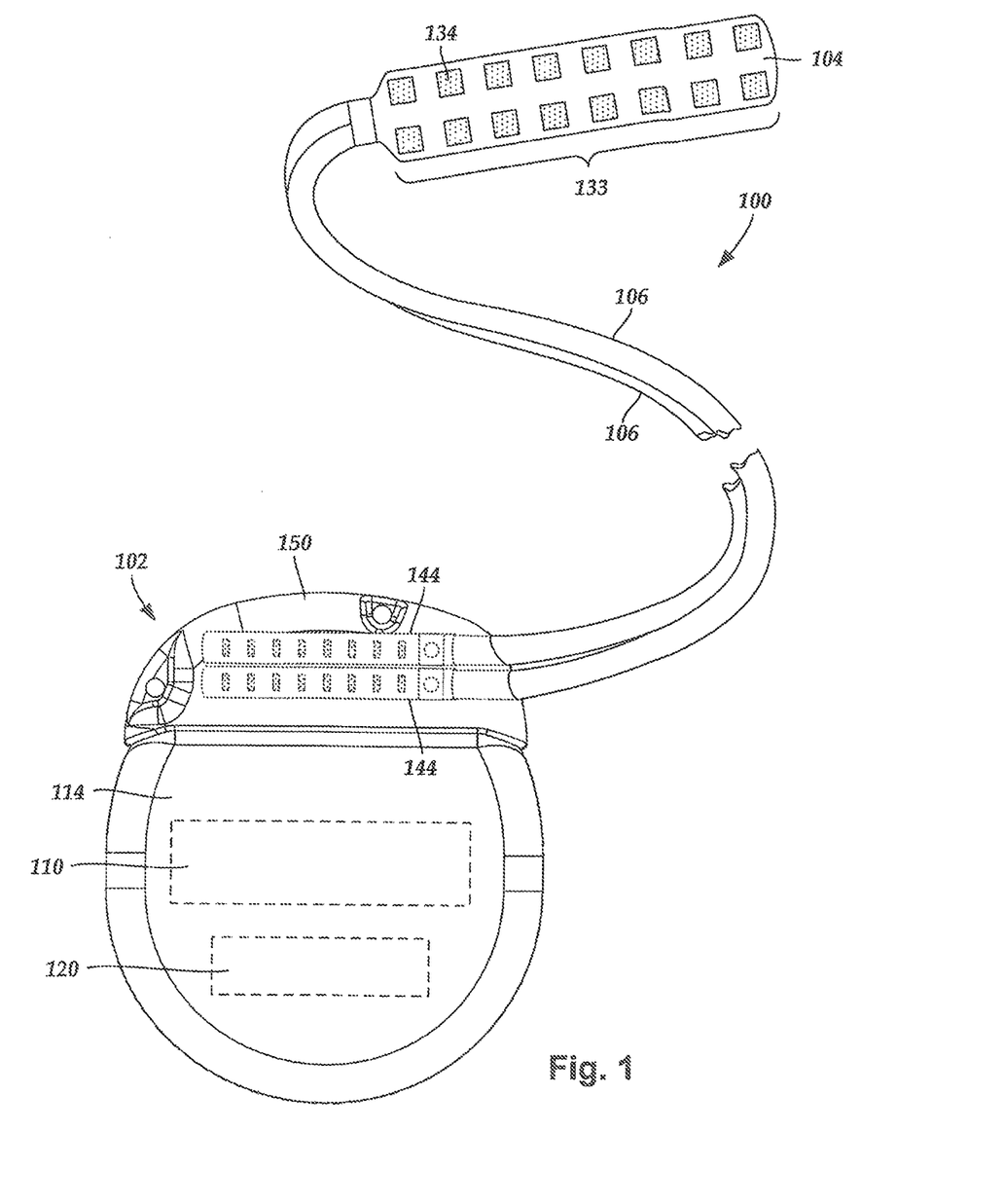
FIG. 1 is a schematic side view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
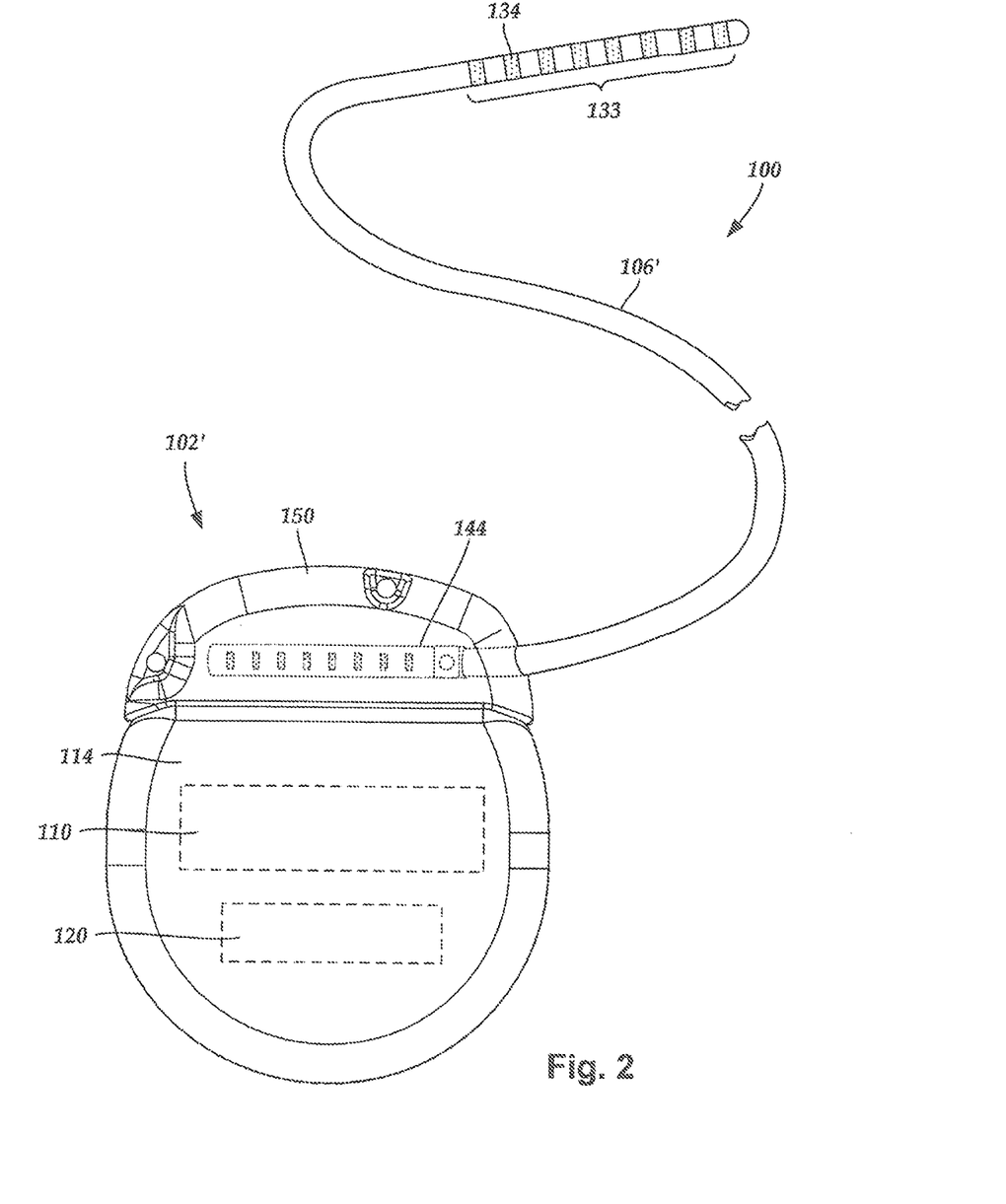
FIG. 2 is a schematic side view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet wire to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
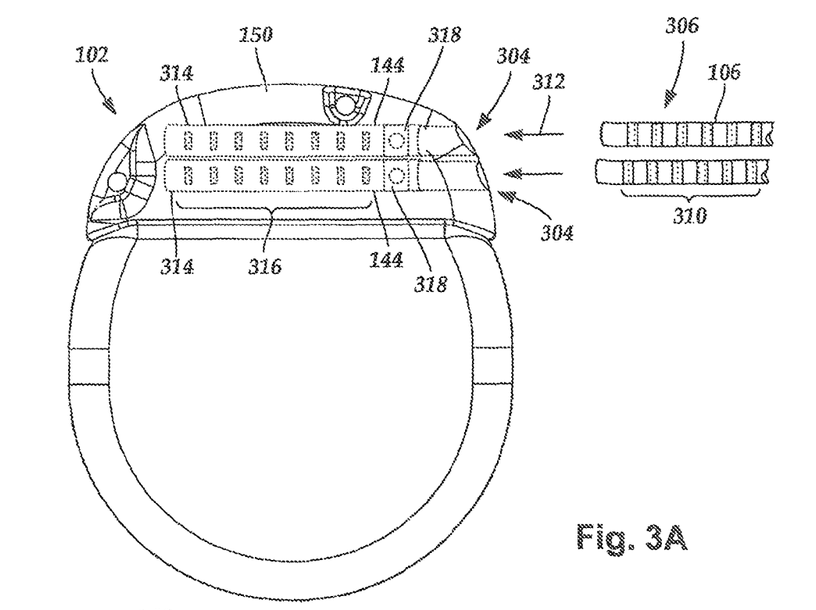
FIG. 3A is a schematic side view of one embodiment of a plurality of connector assemblies disposed in the control module of FIG. 1, the connector assemblies configured and arranged to receive the proximal portions of the lead bodies of FIG. 1, according to the invention.
Figure 3B:
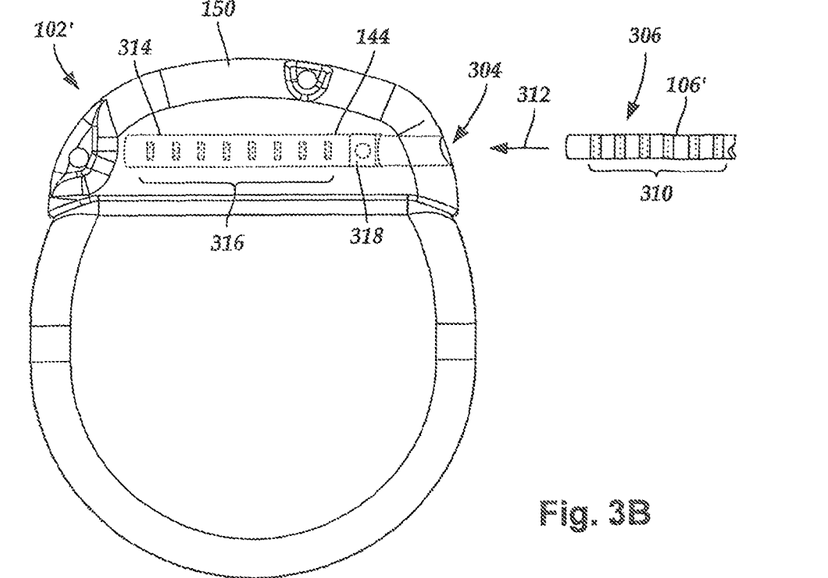
FIG. 3B is a schematic side view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
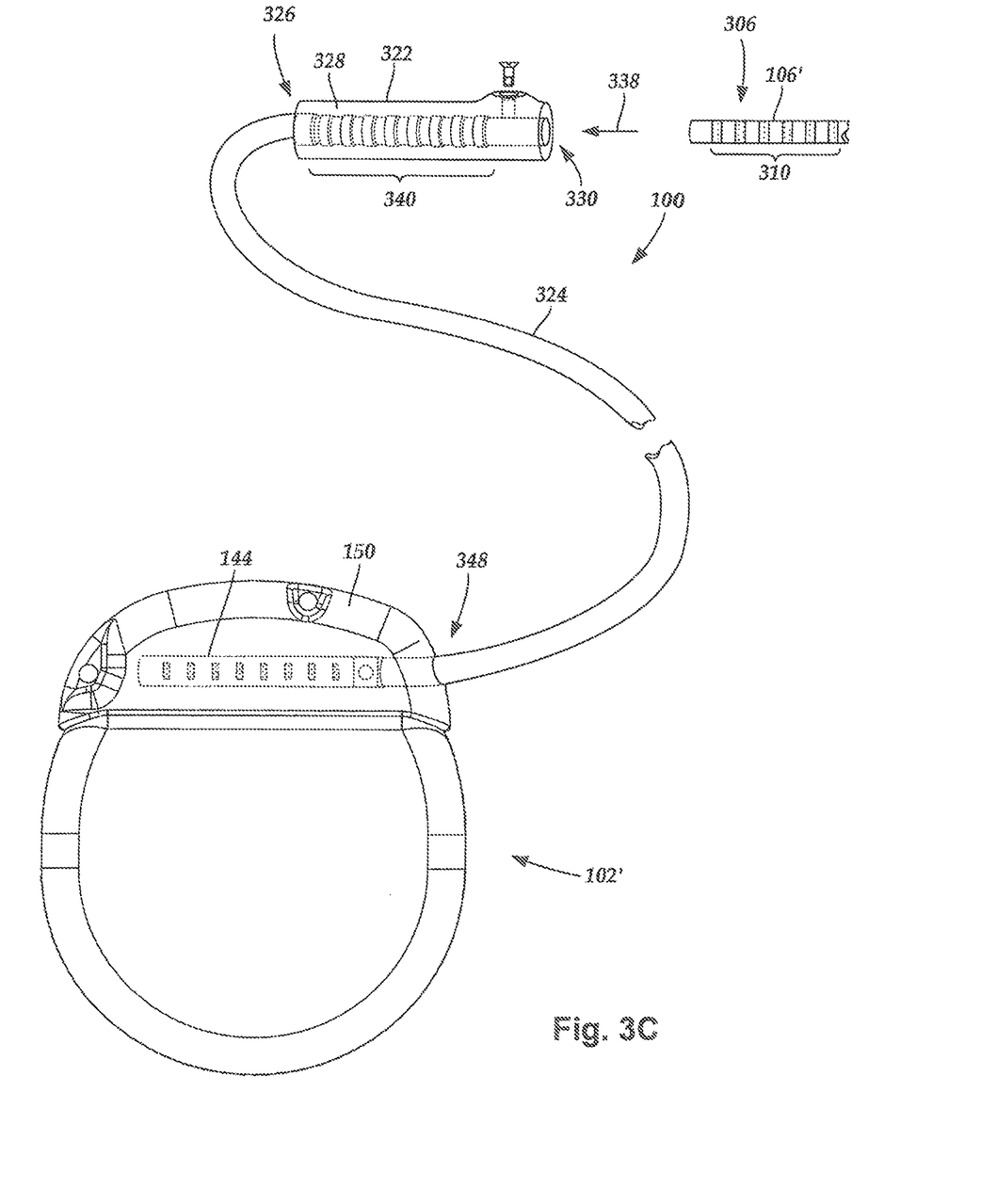
FIG. 3C is a schematic side view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Electromagnetic exposure (such as expected in an MRI environment or other strenuous electromagnetic environments) can result in the lead interacting with the incident fields (especially RF fields) to generate high voltages/currents. The lead captures RF energy and may transmit it to one or both ends of lead with potentially deleterious effects. For example, these high voltages/currents can cause damage to the tissue where the lead is in contact with the tissue by ohmic heating. As another example, the induced voltages and currents can also cause damage to active or passive electronic circuits in the control module (e.g., implantable pulse generator). This kind of electromagnetic (e.g., RF) interaction is expected for any lead with conductive components, especially those with total lengths exceeding 2-3 cm, or with an electrical length in the implanted media exceeding ⅛ wavelength—as such structures can efficiently capture electromagnetic fields.

Several factors can affect the amount of current or voltage induced in the lead such as, for example, applied field strength and character (magnitude and phase), lead design, lead construction, lead shape, lead trajectory, presence of other elements or materials in proximity to the lead, lead length, frequency or frequencies of the RF signal, loading at the un-insulated ends of the lead, the number of leads (for example, two or four leads) and their arrangement (for example, side-by-side or parallel and spaced-apart), and the like. However, it is believed that no comprehensive known method exists to accurately estimate the amount of tissue heating or current flow or other lead responses in a given scenario. Such estimations would be particularly useful when designing, developing, and testing leads.

Current methods for analyzing these effects include exposure testing in phantom or in vitro media (e.g., placing implantable components into a conductive gel in an MRI system), applying RF energy to form a field that interacts with the implantable components, and measuring temperature or local electric fields or currents. Aside from being time consuming and difficult, these measurements are quite coarse, and they only give insight on the conditions under test. Such conditions under test rarely have sufficient complexity of applied field conditions to cover "use case" exposures (since the complexity of applied fields in a human body is significant), and they may give little or no insight on "worst case" scenarios or device performance. Other current methods, such as direct electrical measurements, have often been thwarted due to indeterminate ground position. Theoretical or lump models of leads can be useful, but they tend to involve simplifying assumptions that apply better, or only, to simpler lead constructions or geometries and they must be experimentally validated. The modeling problem becomes particularly complicated if there are multiple wires in the lead.

The present invention is directed to methods, devices, and systems that measure lead response to a series of localized electromagnetic fields, determine a transfer function from the measured responses, and then use the transfer function of a lead to provide useful estimates for lead response to electromagnetic fields. The transfer function, S(z), is the response at a particular point of the lead (for example a stimulation electrode) to the application of excitation (e.g., an electromagnetic field) at other points (e.g., $z_1, z_2, \ldots, z_N$) along the lead. A full transfer function is obtained when the output response to the excitation is measured as excitation is applied over significant segments of the lead, which may include the whole lead length and optionally even areas beyond the lead.

Figure 4:
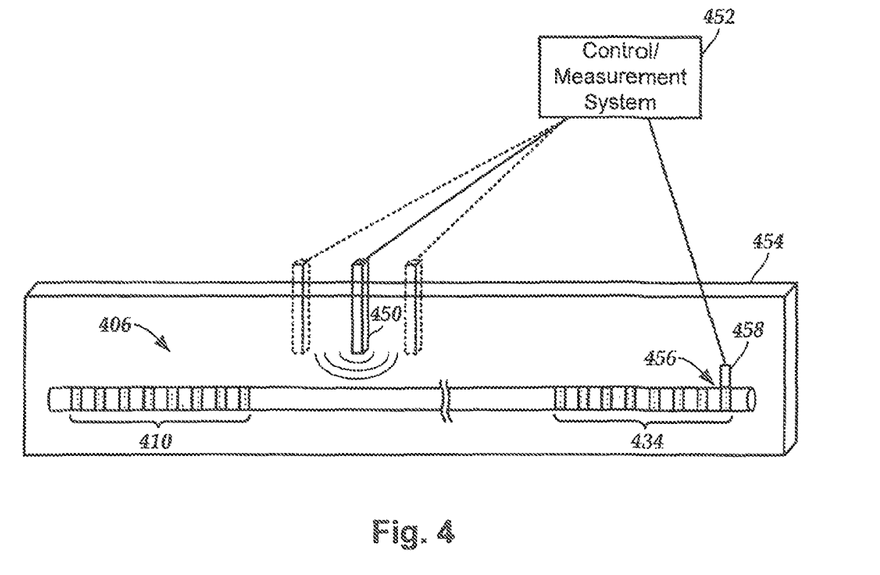
FIG. 4 is a schematic perspective view of one embodiment of a system for determining a transfer function of a lead, according to the invention.

FIG. 4 illustrates one embodiment of an arrangement for estimating a response of a medical lead to an electromagnetic field. The arrangement includes the lead 406, at least one excitation probe 450, and a control/measurement system 452. The lead 406 can be any of the leads described herein or any other medical lead including medical leads used to deliver electrical stimulation to patient tissue (for example, leads such as those for spinal cord stimulation, deep brain stimulation, cardiac pacing, cardiac defibrillation, neurostimulation of other tissues, and so forth). The control/measurement system 452 is coupled to the excitation probe 450 and to at least one portion 456 of the lead 406, such as an electrode 434 or terminal 410. In at least some embodiments, a reception probe 458 (for example, a galvanic connection probe or the like) is provided to directly or indirectly couple the control/measurement system 452 to the portion 456 of the lead. An electromagnetic field excitation is applied using the excitation probe 450 at a distance, z, away from the portion 456 of the lead coupled to the control/measurement system 452. The control/measurement system 452 measures the response to the excitation at the portion 456 of the lead, optionally using the reception probe 458. The transfer function is determined by applying the excitation at a series of distances, $z_1, z_2, \ldots, z_N$, and measuring the response to each excitation.

Alternatively or additionally, a transfer function can be determined by measuring a field at multiple positions along the lead when an excitation (e.g., a current or voltage) is provided at an electrode or terminal of the lead. This can be considered an inverse method of determination of the transfer function.

Alternatively or additionally, a second excitation probe can be used to provide excitation at a second location to at least partially (and, preferably, fully) cancel the effect of excitation probe 450 at the reception probe 458. The transfer function can be determined based on one or more parameters (e.g., current, voltage, power, or the like) of the excitation provided at the second excitation probe. For example, the amount of power or current (or the like) applied using the second excitation probe to cancel the excitation from the excitation probe 450 as determined at the reception probe 458 can be measured and used to determine the transfer function.

In at least some embodiments, the lead 406 is immersed in a phantom medium 454. The transfer function of the lead can vary significantly with the electrical properties of the phantom medium 454. Therefore, in one embodiment of this invention, this medium 454 has similar electromagnetic properties (e.g. dielectric constant, conductivity), at the frequencies of interest, as would be experienced by the lead when located in the human body. The medium 454 can be liquid or solid or any combination thereof.

In some embodiments, the medium 454 may be non-uniform along the length of the lead. For example, portions of the medium 454 may be compartmentalized along the lead so that the portions may have different dielectric constants or conductivities or both. These different portions of the medium may represent spatially changing properties of a body to more accurately model the expected conditions around the lead when implanted within a body.

To measure the transfer function, at least one excitation probe 450 is used to produce an electromagnetic field excitation. The embodiment illustrated in FIG. 4 includes an excitation probe 450 that can be moved to different positions as illustrated in FIG. 4 by the dotted line renditions of the probe to the right and left of excitation probe 450. In at least some embodiments, the medium 454 is a material that allows the excitation probe 450 to move through the medium. In other embodiments, the excitation probe 450 is removed from the medium and then reinserted at another position. In at least some embodiments, the lead is disposed in the medium, but the probe is outside the medium.

Figure 5:
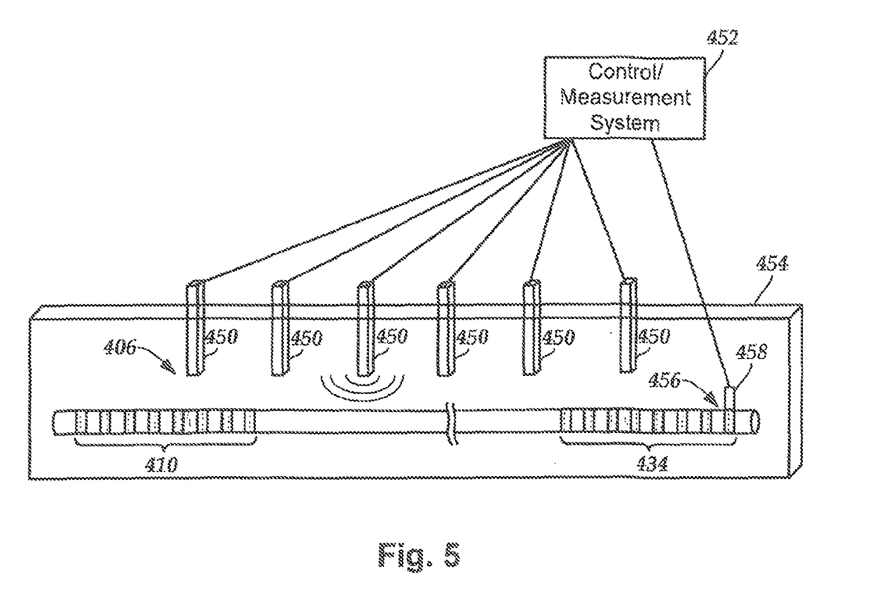
FIG. 5 is a schematic perspective view of another embodiment of a system for determining a transfer function of a lead, according to the invention.

In at least some embodiments, the arrangement may include multiple probes 450, as illustrated in FIG. 5. These probes may be stationary or movable. The probes 450 may be spaced at regular intervals or may be spaced in any other desired regular or irregular pattern.

Any suitable spacing between probe positions (e.g., between probe positions as illustrated in FIG. 4 or probes in FIG. 5) can be used including regular or irregular spacing patterns. The distance between probe positions can be any suitable value including, for example, a value in the range of 1 mm to 5 cm or in the range of 5 mm to 5 cm or in the range of 5 mm to 2 cm.

The electromagnetic field produced at the excitation probe 450 induces signals in the lead 406 which ultimately reach an electrode 434 or terminal 410 (or other portion of the lead 406) to which the control/measurement system 452 is attached. In at least some embodiments, the electromagnetic field excitation generated by the probe is localized to a small section of the lead under test. In at least some embodiments, the excitation probe 450 primarily provides an electric field (in any direction or in a particular direction), a magnetic field (in any direction or in a particular direction), an electric current, an electric voltage, an electric power, or any combination thereof. The excitation can be applied using continuous signals (for example, sinusoidal signals), square waveform signals (e.g., pulsed signals), sinc signals, chirps, or the like.

The signals provided by the excitation probe can contain primarily a single frequency or a single frequency band or multiple frequencies or multiple bands of frequencies. In some embodiments, the excitation probe may provide a sequence of signals at the same frequency/frequencies or frequency band(s), or a sequence of signals at different frequencies or frequency bands, or any combination thereof.

In at least some embodiments, the excitation probe 450 is placed near the object under test. In at least some embodiments, the excitation probe 450 is placed in direct contact with the lead under test or even in electrical contact with the lead under test. In some embodiments, the excitation probe 450 may be a multi-element probe or combination of one or more probes to provide a controlled spatial excitation region (for example, a region of uniform excitation) along a portion of the lead.

In at least some embodiments, a reception probe 458 is provided at the portion 456 to receive or measure a signal (e.g., a current, a voltage, power, or the like) produced at the portion 456 as a result of the electromagnetic field excitation generated by excitation probe 450. The reception probe may be directly coupled to the portion 456 of the lead or may be indirectly (e.g., capacitively or inductively) coupled to the portion 456 of the lead. In at least some embodiments, the reception probe is matched to the expected impedance of the tissue within which a lead would be implanted or to a control module (e.g., implantable pulse generator) to which the lead would be coupled. In at least some embodiments, the reception probe has an impedance that is at least double (or at least triple or at least five times or at least ten times) the expected impedance of the tissue within which the lead would be implanted or to a control module (e.g., implantable pulse generator) to which the lead would be coupled in order to reduce the load effect of the probe.

The excitation probe 450 can be any suitable construction for providing an electromagnetic field and the reception probe 458 can be any suitable construction for receiving signals from the lead. For example, the excitation probe and reception probe can be individually a coaxial cable and BNC connector, an H-field probe, a toroidal probe, a dipole, or the like. The excitation probe and the reception probe may be the same type of probe or different types of probes. The choice of probe type may account for the dominant or preferred coupling mechanism between the electromagnetic field/signal and the lead.

The control/measurement system 452 includes one or more devices that control application of the electromagnetic field through excitation probe 450 and the reception of signals from reception probe 458. These two functions may be performed using a single device or different devices which may or may not be coupled together. The control/measurement system 452 may include a processor (e.g., a computer) for determining the transfer function from the signals received using the reception probe. Alternatively, the control/measurement system 452, or a user, may provide the signal information to a separate processor. The control/measurement system 452 may include one or more interface devices (e.g., keyboard, mouse, media drive or port, touch screen, touch pad, or the like) to receive input from a user. The control/measurement system 452 may also include one or more display devices. The control/measurement system may also include RF generating or RF amplification circuitry or any combination thereof.

It will be understood that the control/measurement system 452 may be coupled at multiple positions along the lead, for example, at multiple electrodes, multiple terminals, or any combination of electrodes and terminals (or even at other positions along the lead). When the control/measurement system is coupled to the lead at multiple positions, the control/measurement system 452 may obtain individual readings at each position, produce a composite reading from two or more of the positions, or any combination thereof. For example, the control/measurement system 452 may generate an electromagnetic field with a desired magnitude and phase pattern along the lead and obtain readings regarding the electrical response or potential heating of tissue due to the generated electromagnetic field.

In at least some embodiments, S(z) of the lead under test can be given as a parameter from a device such as a network analyzer which is a part of the control/measurement system 452. In at least some embodiments, the lead under test is scanned by varying z (i.e., the distance between the excitation probe 450 and the position 456 in FIG. 4) to determine the transfer function along the lead. The transfer function may be determined by testing along the entire length of the lead or a portion of the lead. In some embodiments, the lead under test is scanned in uniform size steps between positions of the excitation probe 450 (or between excitation probes when multiple excitation probes are used, as illustrated in FIG. 5) along the lead. In other embodiments, the step sizes vary along the lead being scanned.

In at least some embodiments, the signals picked up by the reception probe can be averaged to provide a better measurement. In at least some embodiments, the scanning process is performed by an automated system that sweeps across the length of the object under test. In at least some embodiments, the application of the electromagnetic field excitation and the measuring of the resulting signal is done by an automated system which has recording and data processing capabilities. In at least some embodiments, the control/measurement system 452 includes a signal analyzer which may directly provide the transfer function as a ratio of the signal received and the signal sent.

The signals received at by the reception probe in response to the electromagnetic field produced at the excitation probe can be used to determine a transfer function, S(z). The transfer function may be considered a ratio of response to excitation, where (in at least some embodiments) the response, excitation, and transfer function are represented by complex numerical quantities.

Using this transfer function, the total effect of the excitation on any point on the lead can be estimated using, for example, an integration function (or its equivalent). In one embodiment, the power coming out of the lead (for example, at an electrode or terminal) given any electromagnetic field profile can be calculated or estimated. For example, for tangential electric field exposure ($E_{tan}^{inc}$) an estimate of the total voltage, $V_{end}$, at the end of the lead is $$V_{end} = \int_{z=0}^{L} E_{tan}^{inc}(z) S(z) dz$$

where L is the length of the lead, and the power, $\hat{P}$, delivered to a load at a proximal/distal end of the lead is $$\hat{P} = |V_{end}|^2 \mathrm{Re}\left[\frac{1}{Z_{load}}\right] = \eta |V_{end}|^2$$

$$\Rightarrow \hat{P} = \eta \left|\int_{z=0}^{L} E_{tan}^{inc}(z) S(z) dz\right|^2$$

where $Z_{load}$ is the load at the end of the lead.

The transfer function can be used to evaluate a number of different scenarios, such as, for example, a "worst case" scenario which attempts to determine the maximum electrical signal that might be generated at a point on the lead (e.g., at the end of the lead or at an electrode or terminal) in response to an electromagnetic field. In one embodiment, to determine worst case, the following definitions of inner product and norm are used:

$$\langle a, b \rangle = \int_{z=0}^{L} a(z) b^*(z) dz \text{ and } \|a\| = \sqrt{\langle a, a \rangle}$$

Here ( )* denotes the complex conjugate of the quantity. The Cauchy-Schwarz inequality is $$|\langle a, b \rangle|^2 \leq \|a\|^2 \|b\|^2$$

where equality holds if, and only if, b=ka and k is a scalar.

The voltage developed at the end of the lead can be written as an inner product between the incident electric field and transfer function $$V_{end} = \langle E_{tan}^{inc}, S^* \rangle.$$

Invoking the Cauchy-Schwarz inequality, $$\hat{P} = \eta |\langle E_{tan}^{inc}, S^* \rangle|^2 \leq \eta \|E_{tan}^{inc}\|^2 \|S\|^2.$$

Moreover, once S(z) has been determined the worst-case tangential electric field profile, under the condition $$\|E_{tan}^{inc}\|^2 = \int_{z=0}^{L} |E_{tan}^{inc}(z)|^2 dz = E_{norm}^2(L),$$

is given in this embodiment by $$E_{tan,worst}^{inc}(z) = E_{norm}(L) \frac{S^*(z)}{|S(z)|}$$

and, in this embodiment, the worst case power delivered is $$\hat{P}_{worst} = \eta \|S\|^2 E_{norm}^2(L)$$

Tighter upper bounds in clinical settings can be obtained if different sections of the lead go through rapid fluctuations of electric field or multiple media. For example, a tighter bound can be obtained by calculating $\hat{P}_{worst}$ for different sections of the lead piecewise and then adding them up.

$$\hat{P}_{ub} = \eta \|S_1\|^2 E_{norm}^2(L_1) + \eta \|S_2\|^2 E_{norm}^2(L_2) + \ldots + \eta \|S_N\|^2 E_{norm}^2(L_N)$$

where the lead has N sections of length $L_1, L_2, \ldots, L_N$ with transfer functions $S_1, S_2, \ldots, S_N$.

In at least some instances, it may be useful to determine a collective response from two or more electrodes or terminals. This may be particularly useful for leads with multiple electrodes and terminals. For example, it may be useful to determine the total power delivered to tissue surrounding an array of electrodes. Methods of determining a collective response are described. If the reception probe is not directly loading the electrode or terminal (e.g. a galvanic connection), the transfer function can be determined by the method described above for each electrode individually. For example, the power delivered to the tissue from i-th electrode is $$\hat{P}_{Ci} = \eta \left|\int_{0}^{L} E_{tan}^{inc}(z) S_{Ci}(z) dz\right|^2$$

where $S_{Ci}$ is the transfer function of the i-th electrode.

However, if there is direct loading then the electrode or terminal connected to the reception probe may see different impedance. The resulting transfer function may be incorrect as the current/voltage distribution on the lead may be modified due to the altered loading condition. This can be easily remedied by restoring balance to the electrodes. In one embodiment, the rest of the electrodes or terminal can be terminated in dummy loads that have the same value as the impedance of the reception probe. The transfer function of each electrode or terminal can then be measured in turn.

In another embodiment, the transfer functions of all the electrodes or terminals can be measured simultaneously. This can be accomplished by connecting a reception probe to each of the electrodes or terminal and either use multiple measurement systems (e.g. network analyzers), one for each reception probe, or multiplex (e.g. in time domain using relays) the signal received at each reception probe.

One embodiment of interest is if the applied field is uniform in magnitude ($E_0$) along the length. In this scenario, the worst case power generated at an electrode or terminal is given by $$\hat{P}_{worst} = \eta \|S\|^2 E_0^2 L^2$$

which occurs for $$E_{tan}^{inc}(z) = E_0 \frac{S^*(z)}{|S(z)|}$$

This worst case estimate follows from the following inequality $$\hat{P} = \eta \left| \int_{z=0}^{L} E_{tan}^{inc}(z) S(z) dz \right|^2 \leq \eta \left\{ \int_{z=0}^{L} |E_{tan}^{inc}(z)||S(z)|dz \right\}^2 = \eta \|S\|^2 E_0^2 L^2 = \hat{P}_{worst}$$

Figure 6:
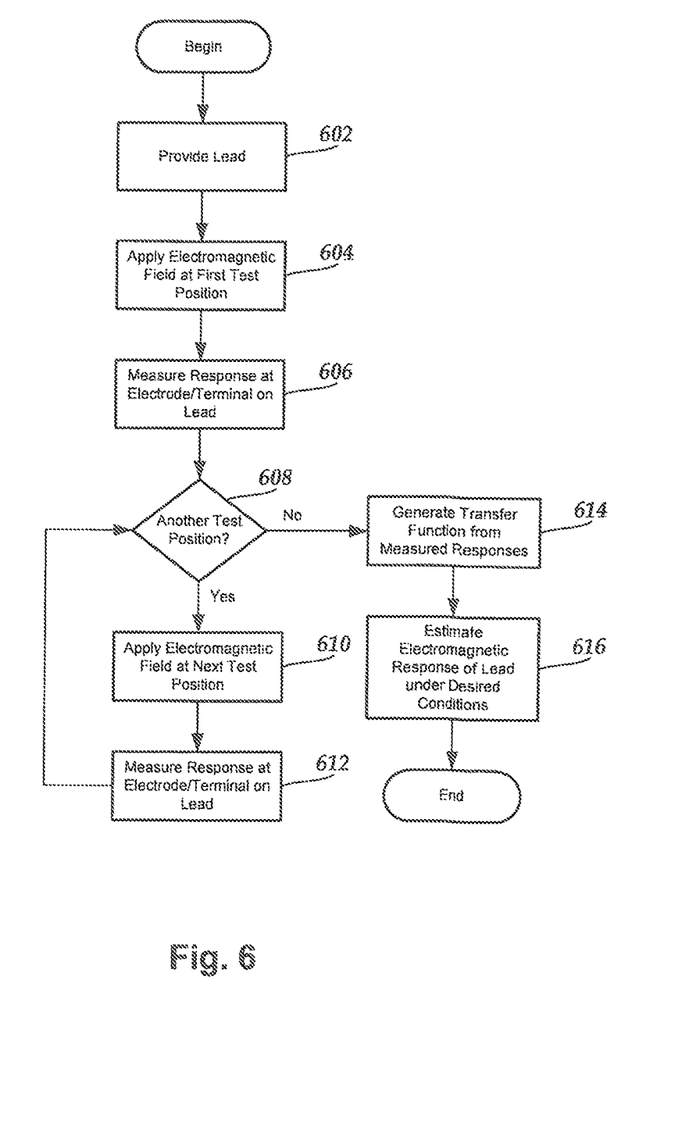
FIG. 6 is a flowchart of one embodiment of a method of estimating a response of a lead to an electromagnetic field, according to the invention.

FIG. 6 illustrates one embodiment of a method for estimating response to an electromagnetic field. In step 602, a lead is provided. Any medical lead or other similar device can be used. The lead is preferably placed in a medium for testing as described above. The lead is coupled to one or more reception probes and one or more excitation probes are also provided. In step 604, an electromagnetic field is applied at a first test position on the lead using the test probe. In step 606, the response to the applied electromagnetic field is measured at the electrode or terminal or other position on the lead to which the reception probe is coupled. In step 608, it is determined whether there is another test position on the lead. If so, steps 610 and 612 include the application of the electromagnetic field at the next test position and the response is measured at the electrode, terminal, or other position on the lead. This is repeated until all test positions have been accessed. In step 614, the transfer function is generated from the measured responses. In step 616, the electromagnetic response of the lead can be estimated using the transfer function as described above. It will be recognized that this method can be modified to account for multiple excitation probes and multiple reception probes. It will also be recognized that steps described above may be performed simultaneously or sequentially, if possible.

Figure 7:
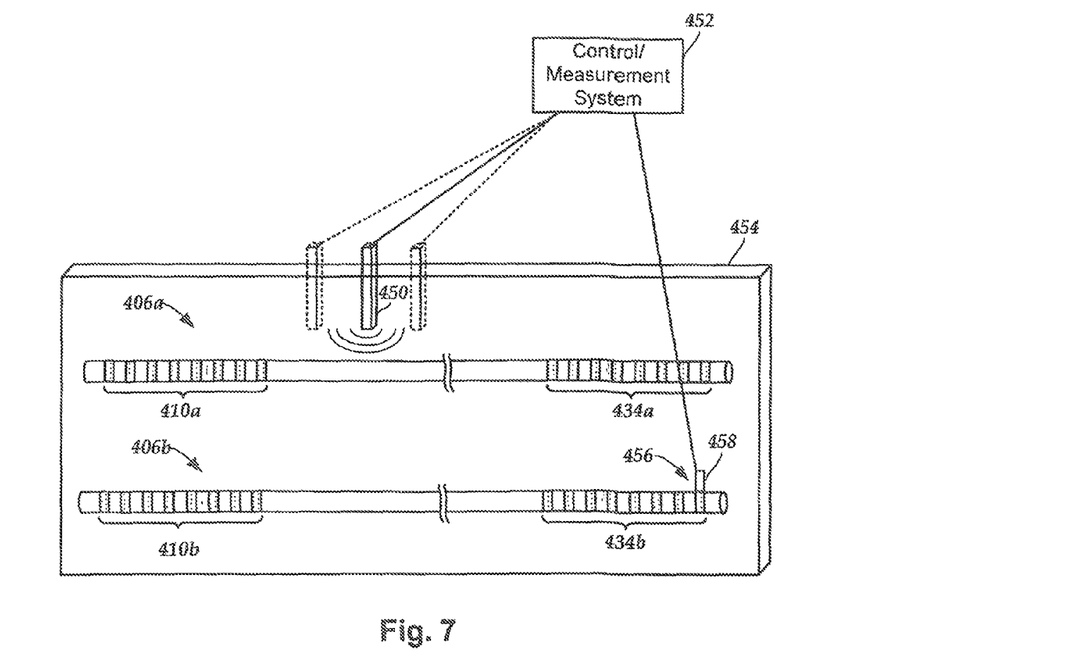
FIG. 7 is a schematic perspective view of one embodiment of a system for determining a transfer function between a first lead and a second lead, according to the invention.

A transfer function can also be determined between two leads. FIG. 7 illustrates one embodiment of an arrangement for estimating a lead-to-lead coupling potential. The arrangement includes a first lead 406a, a second lead 406b, at least one excitation probe 450, a control/measurement system 452, and a reception probe 458. The leads 406a, 406b can be any of the leads described herein or any other medical lead including medical leads used to deliver electrical stimulation to patient tissue (for example, leads such as those for spinal cord stimulation, deep brain stimulation, cardiac pacing, cardiac defibrillation, neurostimulation of other tissues, and so forth) and the leads may be arranged in any manner relative to each other. The control/measurement system 452 is coupled to the excitation probe 450 and to at least one portion 456 of the second lead 406b, such as an electrode 434b or terminal 410b. In at least some embodiments, a excitation probe 450 directly couples the control/measurement system 452 to a portion of the first lead 406a, such as a terminal 410a or electrode 434a so that the excitation signal is injected directly into the first lead 406a. In at least some embodiments, an electromagnetic field excitation is applied to the first lead 406a using the excitation probe 450 without directly coupling to a terminal or an electrode. The control/measurement system 452 measures the response to the excitation at the portion 456 of the second lead 406b using the reception probe 458.

The determined transfer function amplitude may be dependent on factors such as excitation probe construction and relative placement of the excitation probe to a lead being evaluated. The method can be used to compare the response of different leads in a relative sense without establishing an absolute amplitude response factor, e.g. to a radiated environment. Calibration methods may be applied if absolute amplitude response is desired.

It will be understood that each block of the flowchart illustrations, and combinations of blocks in the flowchart illustrations, as well any portion of the control/measurement system, methods of measuring signals, methods of determining a transfer function or of using the transfer function to evaluate a lead, and any other systems and methods disclosed herein, can be implemented by computer program instructions. These program instructions may be provided to a processor to produce a machine, such that the instructions, which execute on the processor, create means for implementing the actions specified in the flowchart block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium (including any non-transitory computer-readable medium) including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

One potential advantage of methods and systems that determine a transfer function is that such a method or system may be used to characterize lead performance over a band of frequencies, in magnitude and phase. Another potential advantage is that the method or system can be applied to any lead design compared to other modeling strategies that may be restrictive. In at least some embodiments, the method or system can be used to estimate worst case heating or current conditions. In some embodiments, the method or system can incorporate excitation functions that are electric fields (e.g., total field, tangential field, perpendicular field, azimuthal field, radial field, or the like), magnetic fields (total, tangential, perpendicular, radial, azimuthal, or the like), or any combination thereof. These excitation functions can be obtained by direct measurement in the medium of interest or by electromagnetic simulations (e.g. FDTD, MoM, FEM, or the like). Another potential advantage is that several types of output measures can be obtained depending on the application, for example, voltage, power, specific absorption rate, temperature, electric fields, magnetic fields, and the like. These output measures could be measured in direct contact with the lead or at a distance from it. These probes could also include other measures such optical fluorescence, any the like or any other parameter that is representative of the effect to measure. The output measures can be measured in amplitude, phase, time domain, frequency domain, spatial gradients, infrared, or the like, as applicable.

An implanted medical lead has been used as an example above. It will be understood that the methods, arrangements and systems described above can be applied to other devices and objects. For example, a transfer function can be determined and used as described above for other implantable medical devices, such as, for example, catheters, guidewires, interventional MRI tools and probes, orthopedic implants, wires, stents, and the like. Transfer functions can also be determined for devices other than medical devices and for non-implanted devices and objects.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of estimating response of a medical lead to an electromagnetic field, the method comprising:
    providing a medical lead having a proximal end, a distal end, at least one electrode disposed along the distal end, at least one terminal disposed along the proximal end, and at least one conductor extending along the medical lead and electrically coupling the at least one electrode to the at least one terminal;
    coupling at least one electrode or at least one terminal of the medical lead to a control/measurement system;
    individually applying a test field at each of a plurality of test positions along the medical lead using at least one excitation probe, wherein each test position corresponds to a position of a one of the at least one excitation probe and each test position is a different distance from the at least one electrode or at least one terminal coupled to the control/measurement system;
    for each application of the test field, determining a response to the application of the test field at the at least one electrode or at least one terminal coupled to the control/measurement system;
    generating a transfer function using a combination of the responses determined for the applications of the test field; and
    using the transfer function to estimate a response of the medical lead to an electromagnetic field.

2. The method of claim 1r wherein using the transfer function to estimate the response of the medical lead comprises using the transfer function to estimate tissue heating when the medical lead is implanted into a body and subjected to a magnetic resonance imaging procedure.

3. The method of claim 1, wherein using the transfer function to estimate the response of the medical lead comprises using the transfer function to estimate an induced electrical signal at one or more of the at least one terminal or at least one electrode when the medical lead is implanted into a body and subjected to a magnetic resonance imaging procedure.

4. The method of claim 3, wherein using the transfer function to estimate an induced electrical signal delivered at one or more of the at least one terminal or at least one electrode comprises using the transfer function to estimate an induced current at one or more of the at least one terminal or at least one electrode.

5. The method of claim 3, wherein using the transfer function to estimate an induced electrical signal at one or more of the at least one terminal or at least one electrode comprises using the transfer function to estimate an induced power at one or more of the at least one terminal or at least one electrode.

6. The method of claim 3, wherein using the transfer function to estimate an induced electrical signal at one or more of the at least one terminal or at least one electrode comprises using the transfer function to estimate a worst case amount of induced power at one or more of the at least one terminal or at least one electrode.

7. The method of claim 3, wherein using the transfer function to estimate an induced electrical signal at one or more of the at least one terminal or at least one electrode comprises using the transfer function to estimate a worst case applied field magnitude and phase at one or more of the at least one terminal or at least one electrode.

8. The method of claim 1, wherein individually applying a test field at each of a plurality of positions along the medical lead using at least one excitation probe comprises sequentially applying a test field at regular intervals along the medical lead using the at least one excitation probe.

9. The method of claim 1, wherein determining a response comprises, for each application of the test field, determining a response to the application of the test field at a plurality of the at least one terminal or at least one electrode.

10. The method of claim 9, wherein generating a transfer function comprises, for each of the plurality of the at least one terminal or at least one electrode for which a response was determined, using a combination of the responses determined for that electrode or terminal to generate a transfer function for that electrode or terminal.

11. The method of claim 10, wherein using the transfer function comprises using a combination of the transfer functions generated for each of the plurality of the at least one terminal or at least one electrode to estimate a response of the medical lead to an electromagnetic field 12. The method of claim 1, further comprising placing the medical lead into a medium that is electromagnetically similar to a region of a body.

13. The method of claim 1, wherein using the transfer function to evaluate the response of the medical lead comprises using the transfer function to estimate a worst case amount of tissue heating when the medical lead is implanted into a body and subjected to a magnetic resonance imaging procedure.

14. A non-transitory computer-readable medium having processor-executable instructions for estimating response of a lead to an electromagnetic field, the processor-executable instructions when installed onto a device enable the device to perform actions, comprising:
    individually applying a test field at each of a plurality of test positions along a medical lead using an excitation probe, wherein at least one electrode or at least one terminal of the medical lead is coupled to a control/measurement system, wherein each test position corresponds to a position of the excitation probe and each test position is a different distance from the at least one electrode or at least one terminal coupled to the control/measurement system;
    for each application of the test field, determining a response to the application of the test field at the at least one electrode or at least one terminal coupled to the control/measurement system;
    generating a transfer function using a combination of the responses determined for the applications of the test field; and using the transfer function to estimate a response of the medical lead to an electromagnetic field.

15. The non-transitory computer-readable medium of claim 14, wherein determining a response comprises, for each application of the test field, determining a response to the application of the test field at a plurality of the electrodes or terminals.

16. The non-transitory computer-readable medium of claim 15, wherein generating a transfer function comprises, for each of the plurality of the electrodes or terminals for which a response was determined, using a combination of the responses determined for that electrode or terminal to Generate a transfer function for that electrode or terminal.

17. A system for estimating response of a medical lead to an electromagnetic field, the system comprising:
  at least one excitation probe configured and arranged for providing a test field;
  at least one response probe configured and arranged for receiving a signal from a lead in response to the test field; and
  a control/measurement system coupled to the at least one excitation probe and at least one response probe, the control/measurement system comprising a processor for executing processor-readable instructions that enable actions, including:
    individually applying a test field at each of a plurality of test positions along a medical lead using the excitation probe, wherein at least one electrode or at least one terminal of the medical lead is coupled to the control/measurement system, wherein each test position corresponds to a position of the excitation probe and each test position is a different distance from the at least one electrode or at least one terminal coupled to the control/measurement system;
    for each application of the test field, determining a response to the application of the test field at the at least one electrode or at least one terminal coupled to the control/measurement system using the at least one response probe;
    generating a transfer function using a combination of the responses determined for the applications of the test field; and
    using the transfer function to estimate a response of the medical lead to an electromagnetic field.

18. The system of claim 17, further comprising a medium that is electromagnetically similar to a region of a body and configured and arranged to receive the medical lead.

19. The system of claim 17, wherein the system comprises a plurality of the excitation probes.

20. The system of claim 17, wherein the system comprises a plurality of the response probes.

21. The system of claim 17, further comprising the medical lead.

22. A method of estimating electromagnetic coupling of a first medical lead to a second medical lead, the method comprising:
  providing a first medical lead and a second medical lead, each having a proximal end, a distal end, a plurality of electrodes disposed along the distal end, a plurality of terminals disposed along the proximal end, and a plurality of conductors electrically coupling the electrodes to the terminals;
  coupling at least one electrode or at least one terminal of the second medical lead to a control/measurement system;
  individually applying a test field at each of a plurality of test positions along the first medical lead using at least one excitation probe without conductive coupling the at least one excitation probe to the first medical lead, wherein each test position corresponds to a position of a one of the at least one excitation probe and each test position is a different distance from the at least one electrode or at least one terminal coupled to the control/measurement system;
  for each application of the test field, determining a response to the application of the test field to the first medical lead at one or more of the electrodes or terminals of the second medical lead coupled to the control/measurement system;
  generating a transfer function using a combination of the responses determined for the applications of the test field; and
  using the transfer function to estimate electromagnetic coupling of the first medical lead to the second medical lead.

* * * * *